United States Patent [19]

Gutbier

[11] Plant 4,384

[45] Feb. 20, 1979

[54] POINSETTIA V-14

[75] Inventor: Gregor Gutbier, Linz, Fed. Rep. of Germany

[73] Assignee: Paul Ecke, Jr., Encinitas, Calif.

[21] Appl. No.: 899,727

[22] Filed: Apr. 24, 1978

[51] Int. Cl.[2] ..... A01H 5/00

[52] U.S. Cl. ..... Plt./86

[58] Field of Search ..... Plt./86

*Primary Examiner*—Robert E. Bagwill

*Attorney, Agent, or Firm*—Chas. W. Rummler

[57] ABSTRACT

A new variety of poinsettia plant distinguished by the unique characteristic of having nearly the overall beauty and red color of Eckespoint C-1 Red (U.S. Plant Pat. No. 2,923) but blooming approximately one to two weeks earlier at about one to two degrees C. lower forcing temperature thereby effecting a considerable saving of fuel. This new plant also has the unique ability to produce a side shoot on its stem for virtually every axial bud thereby adapting this variety for production of multi-stemmed (pinched) plants of superior beauty and quality. The bracts are often as wide as they are long with a remarkable absence of drooping and since the bract petioles are short, the bracts have a full and compact appearance.

1 Drawing Figure

BACKGROUND OF THE NEW PLANT

My new variety of poinsettia plant originated as a sport of one of my seedlings, which I have identified as V-12 (unpatented), resulting from extensive breeding efforts carried on by me at Linz (Rhein), Germany. This sport was discovered by me in the course of my study of various greenhouse cultured seedlings produced by various crosses made by me from time to time; and I selected this particular sport for propagation and test because of its distinctly different appearance and habits.

Propagation of this sport was done by me, in my greenhouse at Linz (Rhein), Germany, by means of cuttings from the parent plant and propagation of the resulting clone, through successive generations, has shown that the novel and distinctive characteristics of the original sport hold true from generation to generation and appear to be firmly fixed. Propagation of this new variety for commercial purposes is now being done at Encinitas, Calif., by means of vegetative cuttings.

DESCRIPTION OF THE DRAWING

My new variety of poinsettia plant is illustrated by the accompanying full color photographic drawing in which the upper view shows the general form of the entire plant in full bloom and the lower view shows a top plan view of the plant to illustrate the compact display and bright red color of the bracts, the color rendition being as nearly true as it is reasonably possible to obtain through conventional professional photographic procedures.

DESCRIPTION OF THE NEW PLANT

The following is a detailed description of this new variety of poinsettia plant with the color designations being stated according to the R.H.S. Colour Chart published by The Royal Horticultural Society of London, England, with collaboration of The British Colour Council.

THE PLANT

Origin: Sport.

Parentage: An unpatented seedling identified as V-12.

Classification:

*Botanic.*—*Euphorbia pulcherrima.*

*Commercial.*—Greenhouse poinsettia.

Form: Shrub.

Height: Medium.

Growth Habit:

*As a single stem.*—Upright and vigorous with self-branching side shoots; may require a growth regulator.

*As a branched plant.*—Upright with very many stems producing a bushy, full appearance.

Growth Rate: Very fast. Rooting occurs in 10 to 15 days under automatic mist and the plant will bloom in about 9 to 10 weeks at a night temperature of 17° to 19° C. during October and November. Under poor light conditions, a somewhat higher temperature may be necessary.

Foliage: Alternate and horizontal, with medium persistence and in normal abundance.

*Leaf Size.*—Medium, about 4 to 6 inches long and about 2½ to 4½ inches wide.

*Leaf Shape.*—Substantially ovate, some with acuminate tip. Most leaves have one or two serrations on each side of the petiole.

*Aspect.*—Upper side — dull with vein indented. Under side — dull with ordinary veining.

*Color.*—Upper side — Dark green, between 146A and 147A. Under side — dark green, near 146B.

*Retention.*—The foliage lasts well when kept at a low room temperature, i.e. below 20° C., and with good light intensity.

Bracts: Generally 15 to 20 in number, in overlapping arrangement with a tight center providing a full effect.

*Size.*—Various, up to 7 inches long and 6 inches wide, some being as wide as they are long.

*Shape.*—Ovate-acuminate with substantially entire margins but with some dentations. Small bracts are elliptic in shape.

*Petioles.*—Quite short, from ¼ inch to about 1 inch long.

*Color.*—Bright Red. Upper side — between 46B and 45B. Under side — near 45C.

*Ribs and Veins.*—Veins are of a light creamy color and protrude from the under side of the bracts.

*Retention.*—Medium persistence similar to that of the Eckespoint C-1 varieties.

This new variety of poinsettia plant has nearly the beauty of the popular Eckespoint C-1 Red (U.S. Plant Pat. No. 2,923) but it has a much greater branching habit and it may be bloomed one to two weeks earlier and at a several degrees lower temperature. The plant is of a medium height, somewhat taller than my variety V-10 (U.S. Plant Pat. No. 4,235), but of a height similar to that of other popular varieties. The cyathia cluster is compact and since the bract petioles are usually very short, the plant provides a full and compact display of color when in full bloom. When grown as a single stem plant, the bracts are larger and more beautiful.

Self branching side shoots from axial buds occur to a greater extent on this new plant than has been observed on other commercial poinsettia varieties. Also, it has been noted that when this plant is improperly fertilized, there is a tendency toward leaves of a lighter green color than would be considered normal.

I claim:

1. A new and distinctive red poinsettia plant substantially as herein shown and described, distinguished by its relatively short blooming time and lower forcing temperatures, its ability to produce a side shoot at substantially every axial bud on its stem, and by its large bracts having very short petioles to provide a full compact appearance in full bloom.

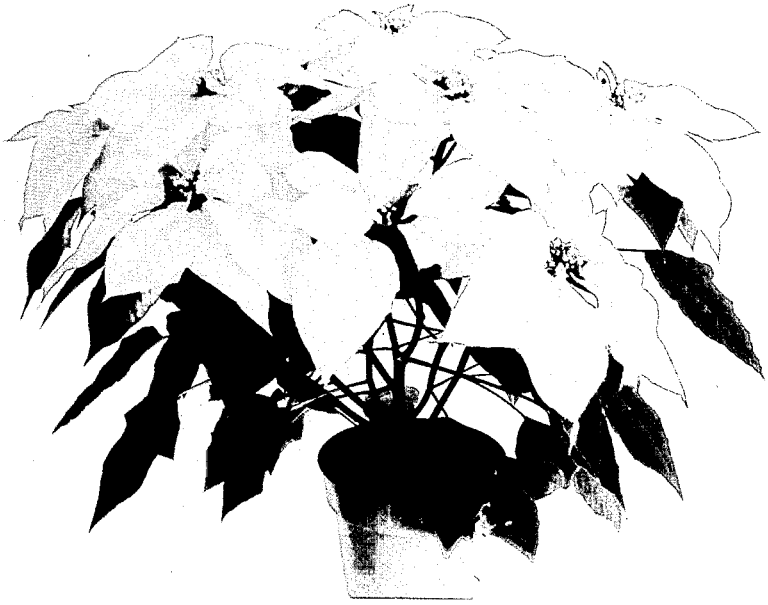
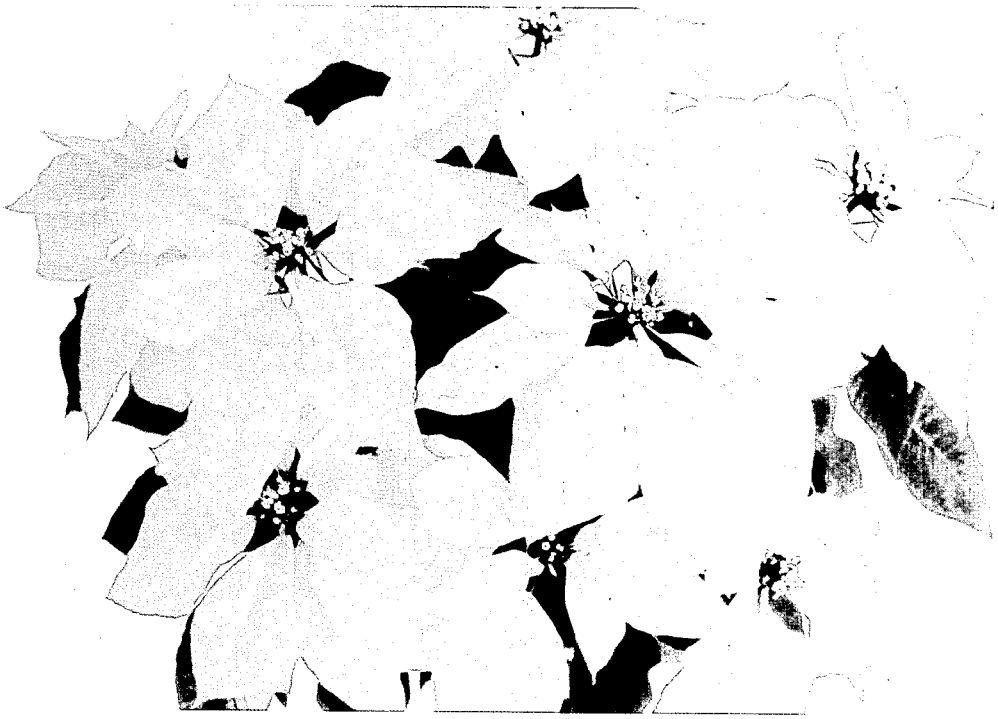

* * * * *